United States Patent [19]

Venderbos

[11] 4,066,693
[45] Jan. 3, 1978

[54] PROCESS FOR THE PREPARATION OF UREA

[75] Inventor: Dirk J. Venderbos, Geleen, Netherlands

[73] Assignee: Stamicarbon, N.V., Geleen, Netherlands

[21] Appl. No.: 284,476

[22] Filed: Aug. 29, 1972

[30] Foreign Application Priority Data

Sept. 2, 1971 Netherlands .......................... 7112061

[51] Int. Cl.$^2$ ............................................ C07C 126/00
[52] U.S. Cl. ................................................ 260/555 A
[58] Field of Search .................................... 260/555 A

[56] References Cited

U.S. PATENT DOCUMENTS

| | | | |
|---|---|---|---|
| 3,090,811 | 5/1963 | Otsuka et al. ......................... | 260/555 |
| 3,105,093 | 9/1963 | Rothkrans ............................. | 260/555 |
| 3,270,051 | 8/1966 | Braun .................................... | 260/555 |
| 3,356,723 | 12/1967 | Kaasenbrood ....................... | 260/555 |

Primary Examiner—James O. Thomas, Jr.
Assistant Examiner—Alan Siegel
Attorney, Agent, or Firm—Cushman, Darby & Cushman

[57] ABSTRACT

A process for preparing urea by the intermediate formation of ammonium carbamate is disclosed, wherein the process involves reduced use of high pressure steam, and the reduced production, as a by-product, of low pressure steam, compared to prior art processes. Ammonium carbamate is formed from ammonia and carbon dioxide in a first reaction zone at a pressure of 90 – 140 atmospheres. Thereafter, the ammonium carbamate is partly converted into urea in a second reaction zone at about the same pressure as the first reaction zone until at least 40% of the equilibrium amount of the urea has formed, and then ammonium carbamate present in the solution from the second reaction zone is converted into additional urea in the third reaction zone at a pressure of at least 160 atmospheres until at least 85% of the equilibrium amount of urea has been formed. The resulting urea synthesis solution is partially expanded and subjected to a stripping treatment, with the gases released in the stripping treatment recycled to the first reaction zone.

7 Claims, 1 Drawing Figure

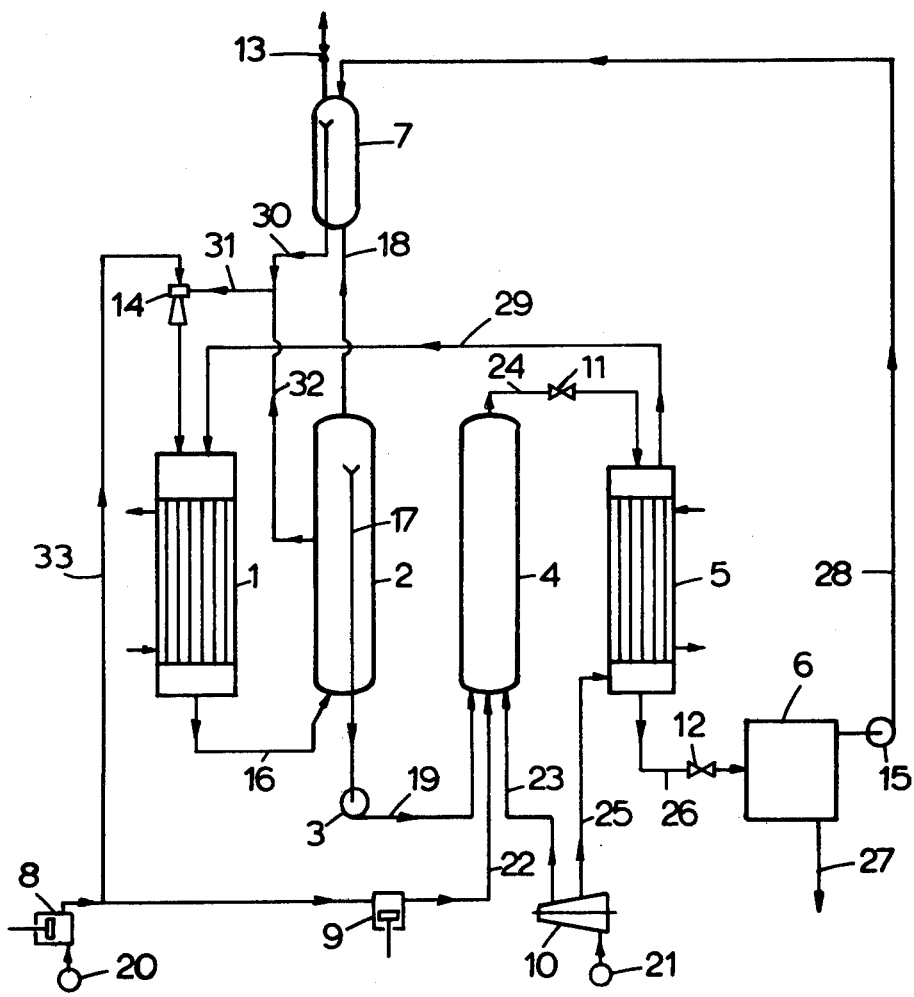

PROCESS FOR THE PREPARATION OF UREA

BACKGROUND OF THE INVENTION

It is known that, under suitable pressure and temperature conditions, urea can be formed from ammonia and carbon dioxide by means of a two-step reaction. The ammonia and carbon dioxide are first reacted to give an ammonium carbamate intermediate product according to the equation

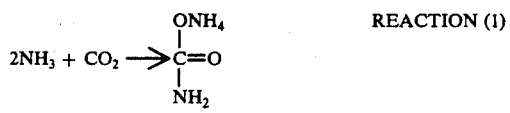

REACTION (1)

Reaction (1) is highly exothermic and proceeds rapidly and to completion if the reaction pressure and temperature are sufficiently high — i.e. above 90 atmospheres and 155° C, respectively.

Urea is formed from the ammonium carbamate by dehydration according to the equation

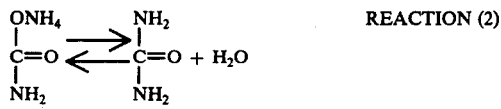

REACTION (2)

Reaction 2, which proceeds endothermically, is an equilibrium reaction wherein the chemical equilibrium is established comparatively slowly, and is shifted towards the right as the pressure and the urea:water ratio are increased.

The prior art conventionally conducted the urea synthesis at a temperature of 160° – 200° C and a pressure of 100 – 250 atmospheres. The urea synthesis solution leaving the urea synthesis zone normally contains unconverted ammonium carbamate. The ammonium carbamate is normally recovered from the urea synthesis solution by decomposition of the ammonium carbamate into gaseous ammonia and carbon dioxide. The decomposition is normally conducted in a number of pressure stages, and the resulting gaseous mixtures of ammonia and carbon dioxide, together with any excess ammonia and the equilibrium amount of water vapor, are separated from the urea synthesis solution. These separated gas mixtures are generally recycled after condensation and/or absorption in water or in an aqueous solution in the above-mentioned pressure stages. Following this recycle process, it will be appreciated that water is necessarily returned to the urea synthesis zone. However, the presence of such water has an adverse effect upon the conversion of ammonium carbamate into urea, and it is therefore desirable to restrict the amount of recycled water as much as possible.

U.S. Pat. No. 3,356,723, issued Dec. 5, 1967, discloses a process for preparing urea wherein the decomposition of the unconverted ammonium carbamate, and the separation of the gaseous mixture from the urea synthesis solution is effected by heating the urea synthesis solution at elevated pressures while a carbon dioxide stripping medium is passed through the urea synthesis solution. The gaseous mixture which is separated from the urea synthesis solution is condensed under elevated pressures with the condensation temperature increasing as the pressure at which the condensation is conducted increases. The heat of condensation may be recovered at a higher temperature level than in earlier processes, and consequently this heat can be used for the production of higher temperature steam. The solidification point of ammonium carbamate is 153° C and in operation at temperatures below this level, the amount of water required to keep the ammonium carbamate in solution (which water is then returned to the urea synthesis zone) is less as the temperature is increased. Preferably, the condensation is conducted in excess of 153° C, as no additional water must then be added. Also, another reason for using the highest possible condensation temperature is that a higher conversion of ammonium carbamate to urea is obtained at higher temperatures. The condensation pressure, however, is limited by the maximum permissible pressure for the stripping operation, since compression of the gas mixture separated in the stripping operation is less undesirable (because of the risk of solid ammonium carbamate depositing in the compressor and conduit lines, and also because of the high cost of compression). The highest permissible stripping pressure is in turn directly related to the temperature level at which the heat of decomposition may be supplied without causing undesirable hydrolysis of urea and biuret formation. The highest permissible stripping pressure is considerably lower than the optimum urea synthesis pressure.

The aforementioned patent suggests, e.g. see FIG. 1 thereof, that the ammonium carbamate solution formed in the condensation zone be pumped to the urea synthesis zone at a pressure which is favorable to the conversion of ammonium carbamate into urea. In this process, all of the heat that is released in the formation of the ammonium carbamate solution in the ammonium carbamate condensation zone is removed by cooling water, and consequently such heat is available only at a low temperature level and thus has limited use. The cooling water is also used to remove heat that is released in the formation of ammonium carbamate from ammonia and carbon dioxide according to Reaction (1). However, the process requires the addition of heat from outside sources for the conversion of ammonium carbamate into urea and for the stripping treatment of the urea synthesis solution, with such heat normally being supplied through high pressure steam (at 15 – 25 atmospheres pressure). It will be appreciated, therefore, that the process of this patent has the drawback that most of the potentially useful heat released during the process is converted into heat having a low economic value — i.e. steam degradation occurs.

SUMMARY OF THE INVENTION

The present invention relates to an improvement in a process for preparing urea by reacting ammonia and carbon dioxide to form ammonium carbamate in a first reaction zone, and then converting ammonium carbamate into urea in a subsequent reaction zone, with partial expansion and stripping of the resulting urea synthesis solution, with the gases released in the stripping treatment separated and recycled to the ammonium carbamate formation zone. The present invention is directed to reducing the process requirements for high pressure steam, and producing less low pressure steam as a by-product of the process. This is achieved by conducting the formation of ammonium carbamate in a first reaction zone in a pressure of 90 – 140 atmospheres and thereafter partly converting the ammonium carbamate into urea in a second reaction zone at about the same pressure as in the first reaction zone until at least 40% of the equilibrium amount of urea has been formed, and then converting ammonium carbamate present in the synthesis solution from the second reaction zone into additional urea in a third reaction zone at a pressure of at least 160 atmospheres until at least 85% of the equilibrium amount of urea that can be obtained in this zone has been formed.

DESCRIPTION OF THE INVENTION

The present invention provides a process for preparing urea from ammonia and carbon dioxide wherein the extent of steam degradation obtained by prior processes, such as the process of U.S. Pat. No. 3,356,723 acknowledged above, is substantially reduced. The present process involves the formation of urea from ammonium carbamate in two different pressure stages, with the respective pressures chosen such that a higher conversion efficiency is obtained than in the process of the aforesaid patent.

The present invention is directed to an improvement in the prior art process for preparing urea wherein ammonia carbamate is formed from ammonia and carbon dioxide in a first reaction zone at a suitable temperature and pressure, thereafter the ammonium carbamate is partly converted into urea in a following reaction zone at a higher pressure, the resulting urea synthesis solution, after being partially expanded, is subjected to a stripping treatment, and the stripped gases are recycled to the first reaction zone. The improved process of the present invention includes converting ammonia and carbon dioxide into ammonium carbamate in the first reaction zone at a pressure of 90 – 140 atmospheres, partly converting the ammonium carbamate into urea in a second reaction zone at substantially the same pressure until at least 40% of the equilibrium amount of urea has been formed. Then the solution obtained in the second reaction zone is passed to a third reaction zone wherein the formation of urea is continued, at a pressure of at least 160 atmospheres, until at least 85% of the equilibrium amount of urea that can be obtained in this third reaction zone has been formed.

The use of the two pressure stage urea synthesis of the present invention allows a considerable portion, e.g. more than half, of the total amount of urea to be formed at a comparatively low pressure, so that the heat needed for this conversion of ammonium carbamate into urea can be supplied at a comparatively low temperature level, with the result that less valuable heat, e.g. steam of lower pressure, can be used. Preferably, the heat required for this portion of the urea formation is supplied from the heat released in the condensation of the gas removed in the stripping zone, by partially conducting the condensation in the second reaction zone. This heat may therefore be utilized directly, with no need for a conversion into low pressure steam. The surplus production of low pressure steam in the urea process is thus considerably reduced, which is a decided advantage if there is an insufficient requirement for this low pressure steam outside of the urea plant.

The amount of heat needed in the third reaction zone for the additional conversion of ammonium carbamate into urea is preferably obtained by converting additional ammonia and carbon dioxide into ammonium carbamate in this reaction zone. The ammonia and carbon dioxide ratios in the process of the present invention may be controlled by the method disclosed in copending application Ser. No. 41,163, the disclosure of which is hereby incorporated by reference for the disclosure of such control method therein, as well as the disclosure of the desired ammonia and $CO_2$ molar ratios and other process parameters therein. The disclosure of U.S. Pat. No. 3,356,723 is also incorporated by reference herein for the disclosure of process conditions for process operations other than the conversion of ammonium carbamate into urea.

Because the stripping treatment, the condensation of the stripped gas mixture, and a portion of the urea synthesis are conducted at a comparatively low pressure according to the present invention, the construction of the process apparatus, including conduits and the like, may be lighter and therefore cheaper. However, the pressure in the first reaction zone (the ammonium carbamate condenser) is high enough that the heat of condensation of the gas mixture fed to this zone becomes available at a temperature level such that the production of useful low pressure steam (of 2 – 5 atmospheres pressure) is possible. The total required volume of the urea synthesis autoclaves remains substantially the same as that of the prior art processes acknowledged hereinabove. Another significant advantage of the present process is that less ammonium carbamate must be decomposed, since higher conversion efficiencies to urea are obtained at the higher pressure in the third reaction zone. Because of this reduced amount of ammonium carbamate in the urea synthesis solution, and also because part of the unconverted ammonia and carbon dioxide is released in the expansion of the urea synthesis solution from the high pressure urea reactor to a lower pressure, a smaller heat exchanger area may be used in the stripping column, and less high pressure steam is needed for the stripping step, than in prior processes.

With a more efficient stripping step, less ammonium carbamate will be retained in the stripped urea synthesis solution, so that the low pressure recycle stage, wherein ammonium carbamate in the stripped urea synthesis solution is decomposed, and the resulting gases are separated and condensed, may also be of reduced size. The stripping treatment may be conducted at a lower temperature, which reduces the corrosive nature of the material in the stripping column, with the result that the structural material in the stripping column may be of a less corrosion-resistant nature, and therefore cheaper. The condensation apparatus for the gas mixture removed in the stripping column may also have a smaller heat exchanger area, as the amount of gas which is to be condensed is less.

DESCRIPTION OF THE DRAWING

The invention will be more clearly understood with reference to the accompanying drawing, wherein a schematic flow diagram of the process of the present invention is illustrated. In the drawing, major process equipment includes ammonium carbamate condenser 1, low pressure urea reactor 2, pump 3, high pressure urea reactor 4, stripping column 5, low pressure recycle stage 6, scrubbing column 7, ammonia pumps 8 and 9, carbon dioxide compressor 10, reducing valves 11, 12 and 13, ejector 14, and pump 15.

In the ammonium carbamate condenser 1, an ammonium carbamate solution is formed at a pressure of 90 – 140 atmospheres and a temperature of 150° to 173° C. This solution still contains considerable amounts of gaseous ammonia and carbon dioxide, generally 20 – 40% of the amounts supplied to ammonium carbamate condenser 1. At the ammonium carbamate solution formation pressure range mentioned above, the heat of condensation in ammonium carbamate condenser 1 is released at such a temperature level that it can be used for the production of low pressure steam.

The gas-liquid mixture formed in ammonium carbamate condenser 1 is introduced into low pressure urea reactor 2 via conduit 16. In low pressure urea reactor 2, which is also operated at a pressure of 90 - 140 atmospheres, a portion of the ammonium carbamate is converted into urea. The heat required for this conversion is preferably obtained by forming additional ammonium carbamate from the gaseous $NH_3$ and $CO_2$ still present. Following this procedure, the amount of gas which is to be condensed in the form of ammonium carbamate, and the retention time in the low pressure urea reactor 2, are selected so that, at the given conditions prevailing in the reactor, urea is produced in an amount corresponding to 40 - 90% of the equilibrium amount. Alternatively, it is possible to fully condense the gas mixture as ammonium carbamate in ammonium carbamate condenser 1, and to transfer part of the condensation heat indirectly to low pressure urea reactor 2 by way of an intermediate heat exchange system, or even to supply all, or only a portion, of the heat required in low pressure urea reactor 2 from external sources. It will be readily appreciated, however, that these alternatives are decidedly less attractive than the preferred embodiment mentioned above.

An aqueous solution of urea, unconverted ammonium carbamate, and uncombined ammonia is discharged into overflow conduit 17 from low pressure urea reactor 2. The upper part of low pressure urea reactor 2 has vent conduit 18 for the discharge of a gas mixture from low pressure urea reactor 2. The gas mixture is substantially uncondensable gases, which have been introduced into the process as impurities in the fresh ammonia gas and carbon dioxide gas. This vented gas mixture is passed through vent conduit 18 into scrubbing column 7, wherein any ammonia and carbon dioxide contained in the gas are recovered, with residual gas vented through reducing valve 13.

The low pressure urea synthesis solution from low pressure urea reactor 2 is passed, by means of pump 3, through conduit 19 into high pressure urea reactor 4, at a pressure of 160 - 300 atmospheres, preferably 180 - 240 atmospheres. The high pressure urea reactor 4 is supplied with fresh ammonia, from a source of supply 20, which is raised to the required pressure by means of pumps 8 and 9, and with fresh carbon dioxide from a source 21, with the carbon dioxide compressed to the required pressure by means of compressor 10. The $NH_3$ and $CO_2$ are supplied to the reactor through conduits 22 and 23, respectively. The high pressure urea reactor is operated at a temperature of from 190° to 220° C, and this temperature is maintained by using the heat released in the formation of ammonium carbamate from the ammonia and carbon dioxide introduced into the reactor. The amount of $NH_3$ and $CO_2$ supplied to high pressure urea reactor 4 can be varied, which varies the amount of heat released from ammonium carbamate formation, which in turn controls the temperature of the high pressure urea reactor 4, under the given reactor pressure and retention times used, so that the urea production is at least 85% of the equilibrium amount for the system in the high pressure urea reactor 4. To accomplish this urea production, the amount of carbon dioxide supplied through line 23 generally amounts to about 10 - 15% of the total amount needed in the process, and the amount of ammonia supplied through line 22 is generally about 40 - 60% of the total amount required in the process.

The high pressure urea synthesis solution leaving reactor 4, containing urea, ammonium carbamate, water, and free ammonia, is expanded in conduit 24 by means of reducing valve 11 to approximately the pressure of the ammonium carbamate condenser 1 and low pressure urea reactor 2, and is then introduced into the top of stripping column 5, which is generally operated at an inlet temperature of 170°- 185° C. The high pressure urea synthesis solution flows down stripping column 5 through vertical pipes in countercurrent flow to a stripping medium, which is preferably carbon dioxide supplied through conduit 25 from a medium-pressure stage of carbon dioxide compressor 10. The vertical pipes in stripping column 5 are heated by high pressure steam, e.g. by steam at a pressure of 15 - 25 atmospheres. The stripped urea synthesis solution is discharged from stripping column 5 through conduit 26, wherein its pressure is reduced by passage through reducing valve 12 to a pressure of less than 6 atmospheres, such as, for instance, 2 - 4 atmospheres, and then the stripped solution is subjected to conventional treatment, such as, for instance rectification, in low pressure stage 6 to remove ammonium carbamate contained in the solution. The aqueous urea solution obtained as a product is discharged through conduit 27, and may be processed further by conventional methods, such as by evaporation or crystallization, to product urea. The diluted ammonium carbamate solution removed in low pressure stage 6 is passed through conduit 28, wherein pump 15 raises the pressure to substantially the pressure of the ammonium carbamate condenser 1 and the low pressure urea reactor 2, to scrubbing column 7, wherein the diluted ammonium carbamate solution serves as a scrubbing liquid for the vent gases supplied through conduit 18.

The gas mixture stripped from the high pressure urea synthesis solution in stripping column 5 (this gas mixture consists of ammonia, carbon dioxide, water vapor and inert gases) collects in the top of that column and is passed through conduit 29 to ammonium carbamate condenser 1, where, as mentioned above, preferably a partial condensation of ammonium carbamate is effected. In order to effect the ammonium carbamate condensation, or formation, at the highest possible temperature level, the diluted ammonium carbamate solution discharged from scrubbing column 7 is introduced into ammonium carbamate condenser 1 by way of conduits 30 - 31. To accomplish this diluted ammonium carbamate flow, use is made of ejector 14, wherein the suction is obtained by way of the $NH_3$ supplied through pump 8 and conduit 33. The amount of ammonia supplied through conduit 33 to control the ammonia-carbon dioxide ratio that is desired for the optimum condensation temperature in ammonium carbamate condenser 1. The ammonia-carbon dioxide ratio may be conveniently monitored by the process described in copending application Ser. No. 41,163, acknowledged above. It is also possible to withdraw a certain amount of urea-ammonium carbamate solution from low pressure urea reactor 2 through conduits 32, 31, by use of ejector 14, according to the process described in copending application Ser. No. 147,055 and this approach also allows an increased condensation temperature in ammonium carbamate condenser 1 to be obtained. Thus, steam of the highest possible pressure and temperature is produced in the operation of ammonium carbamate condenser 1.

EXAMPLE OF THE INVENTION

The invention will be understood more readily by reference to the following example; however, this example is intended to illustrate the invention and is not to be construed to limit the scope of the invention.

In the following example, references to weights are in terms of amounts per day.

100 tons per day of urea were prepared by the process described hereinafter, using the equipment shown schematically on the accompanying drawing (reference to process equipment in this example will be to the corresponding figures of the drawing). To produce this amount of urea, 56.6 tons of $NH_3$ and 73.4 tons per day of $CO_2$ were required.

The ammonium carbamate condenser 1, the first urea reactor (the low pressure reactor) 2 and the stripping column 5 were operated at 110 atmospheres pressure, and the second urea reactor (the high pressure reactor) 4 was operated at 180 atmospheres. A gas-liquid mixture was formed in ammonium carbamate condenser 1 at a pressure of 110 atmospheres and a temperature of 168° C. This mixture, after recalculation to terms of starting ingredients, consisted of (ignoring inert material):

123.8 tons of $NH_3$
115.2 tons of $CO_2$
18.0 tons of $H_2O$. Over 15% of the $NH_3$ and $CO_2$ in the mixture was in the gaseous state. This mixture was introduced into the low pressure urea reactor 2, which was operated at a temperature of 172° C, wherein additional $NH_3$ and $CO_2$ condensed to form ammonium carbamate and 63 tons of urea were formed by conversion of ammonium carbamate. This amount of urea corresponded to over 70% of the equilibrium amount and 63% of the total production. The urea synthesis solution formed in low pressure reactor 2, which had the following composition 63 tons of urea
75 tons of $NH_3$
58.1 tons of $CO_2$
36.9 tons of $H_2O$ was pumped into high pressure urea reactor 4, wherein another 37 tons of urea were formed by conversion of ammonium carbamate at a temperature of 195° C. The heat required for this additional ammonium carbamate conversion into urea was obtained by forming additional ammonium carbamate in high pressure reactor 4 from fresh $NH_3$ and $CO_2$, which were supplied through line 22 and 23, respectively, in amounts of 29 tons and 11 tons, respectively. The total amount of urea discharged from high pressure urea reactor 4 corresponded to more than 95% of the equilibrium amount of urea. The urea synthesis solution discharged through conduit 24 had the composition 100 tons of urea
83 tons of $NH_3$
42 tons of $CO_2$
48 tons of $H_2O$.

This urea synthesis solution also contained slight amounts of inert gases and slight amounts of unmeasured gaseous $NH_3$ and $CO_2$.

The urea synthesis solution was reduced in pressure to 110 atmospheres by passage through reducing valve 11, and was then introduced into stripping column 5, wherein the solution was stripped at a temperature of 176° C with 62.4 tons of $CO_2$ supplied through line 25. The resulting stripped solution had the following composition:

100 tons of urea
10 tons of $NH_3$
13 tons of $CO_2$
44.1 tons of $H_2O$.

The gas mixture from stripping column 5 was recycled to ammonium carbamate condenser 1 by way of line 29. This gas mixture had the following composition:

73.0 tons of $NH_3$
91.4 tons of $CO_2$
3.9 tons of $H_2O$
+ inert material.

Ammonium carbamate condenser 1 was supplied with 27.6 tons of $NH_3$ by way of line 33 and ejector 14. The ejector drew in dilute ammonium carbamate solution formed in scrubbing column 7, by way of lines 30 - 31, which solution had the following composition 23.2 tons of $NH_2$
23.8 tons of $CO_2$
14.1 tons of $H_2O$.

The stripped urea synthesis solution from stripping column 5 was discharged through line 26 and passed through reducing valve 12, wherein the pressure was reduced to 3.5 atmospheres, and then supplied to low pressure recycle stage 6, which was operated at a temperature of 75° C. The ammonium carbamate still in the stripped urea synthesis solution was removed by rectification. The diluted ammonium carbamate solution formed in recycle stage 6 was supplied to scrubbing column 7 by way of line 28, after passing through pump 15 wherein the solution pressure was raised to 110 atmospheres. Product urea solution was discharged through line 27. This solution had the following composition:

100 tons of urea
31.5 tons of $H_2O$.

The low pressure urea reactor 2 and the high pressure urea reactor 4 both operated under virtually adiabatic conditions, with no heat supplied or removed by external means. Stripping column 5 was heated by means of 77.5 tons of saturated steam having a pressure of 22 atmospheres gauge.

In operation, the ammonium carbamate condenser 1 required external cooling and the heat liberated in the ammonium carbamate condenser 1 was used to produce 100 tons of steam having a 3 atmosphere gauge. 80 - 90 tons of this low pressure steam could be used in the low pressure recycle stage 6 and in final processing of the aqueous urea solution, so that the surplus of the low pressure steam was only 10 - 20 tons per day.

The overall process required only 775 kilograms of high pressure steam (25 atmospheres gauge) for each ton of urea produced, while only 100 - 200 kilograms of low pressure steam (3 atmospheres gauge) was produced as a by-product per ton of urea produced, and this low pressure steam was available for other purposes.

What is claimed is:

1. In a process for preparing urea by reacting ammonia and carbon dioxide to form an ammonium carbamate intermediate product in a first reaction zone, and then converting ammonium carbamate into urea in an additional reaction zone at a higher pressure, partially expanding the resulting urea synthesis solution and subjecting the urea synthesis solution to a stripping treatment, and separating gases released in the stripping treatment and from the urea synthesis solution and recycling the separated gases to the first reaction zone, the improvement comprising conducting the formation of ammonium carbamate from ammonia and carbon dioxide in said first reaction zone at a pressure of 90 – 140 atmospheres and a temperature of about 150° to 173° C, thereafter partly converting the ammonium carbamate into urea in a second reaction zone at substantially the same pressure as said first reaction zone and a temperature of about 165 to 183° C until at least 40% of the equilibrium amount of urea has been formed, and thereafter converting ammonium carbamate present in the synthesis solution from the second reaction zone into additional urea in a third reaction zone at a pressure of at least 160 atmospheres and a temperature of about 190° to 220° C until at least 85% of the equilibrium amount of urea that can be obtained in this zone has been formed.

2. Process according to claim 1, wherein from 70 – 95% of the equilibrium amount of urea is formed in said second reaction zone.

3. Process according to claim 1, wherein carbon dioxide is incompletely converted into ammonium carbamate in the first reaction zone and at least most of the unconverted carbon dioxide is converted into ammonium carbamate in the second reaction zone, whereby the heat of ammonium carbamate formation in said second reaction zone supplies substantially all the heat required for urea formation in said reaction zone.

4. Process according to claim 1, wherein substantially all the heat required for the formation of urea in said third reaction zone is supplied by forming additional ammonium carbamate in said third reaction zone from ammonia and additional carbon dioxide.

5. Process according to claim 1, wherein the pressure in said third reaction zone is 160 – 300 atmospheres.

6. Process according to claim 1, wherein the pressure in said third reaction zone is 180 – 200 atmospheres.

7. Process according to claim 1, wherein ammonium carbamate is converted into urea in said second reaction zone in an amount corresponding to about 40 – about 90% of the equilibrium amount of urea.

* * * * *